United States Patent [19]

Davila et al.

[11] Patent Number: 5,520,655
[45] Date of Patent: May 28, 1996

[54] CATHETER HEMOSTASIS VALVE

[75] Inventors: Luis A. Davila, Cooper City; Carlo R. De La Mata, North Miami Beach, both of Fla.

[73] Assignee: Cordis Corporation, Miami Lakes, Fla.

[21] Appl. No.: 275,828

[22] Filed: Jul. 15, 1994

[51] Int. Cl.⁶ .......................... A61M 39/20; A61M 39/26
[52] U.S. Cl. ............................................. 604/167; 604/256
[58] Field of Search ........................ 604/167, 256

[56] References Cited

U.S. PATENT DOCUMENTS

| | | |
|---|---|---|
| 4,000,739 | 1/1977 | Stevens . |
| 4,421,296 | 12/1983 | Stephens . |
| 4,424,833 | 1/1984 | Spector et al. . |
| 4,568,336 | 2/1986 | Cooper . |
| 4,798,594 | 1/1989 | Hillstead . |
| 4,842,591 | 6/1989 | Luther . |
| 4,895,565 | 1/1990 | Hillstead . |
| 4,909,798 | 3/1990 | Fleischhacker et al. . |
| 4,946,133 | 8/1990 | Johnson et al. . |
| 4,950,257 | 8/1990 | Hibbs et al. . |
| 5,000,745 | 3/1991 | Gurst et al. ............................ 604/167 |
| 5,041,095 | 8/1991 | Littrell ................................... 604/256 |
| 5,064,416 | 11/1991 | Newgard et al. ..................... 604/256 |
| 5,114,408 | 5/1992 | Fleischhacker et al. ............. 604/167 |
| 5,149,327 | 9/1992 | Oshiyama ............................. 604/167 |
| 5,167,637 | 12/1992 | Okada et al. ......................... 604/256 |
| 5,176,652 | 1/1993 | Littrell ................................... 604/256 |
| 5,203,774 | 4/1993 | Gilson et al. . |
| 5,207,656 | 5/1993 | Kranys ................................... 604/167 |
| 5,254,097 | 10/1993 | Schock et al. . |
| 5,267,966 | 12/1993 | Paul ....................................... 604/256 |
| 5,324,271 | 6/1994 | Abiuso et al. . |
| 5,350,363 | 9/1994 | Goode et al. ......................... 604/256 |
| 5,453,095 | 9/1995 | Davila et al. . |

Primary Examiner—Paul J. Hirsch
Attorney, Agent, or Firm—Gerstman, Ellis & McMillin, Ltd.

[57] ABSTRACT

A catheter which carries a hemostasis valve, such as a catheter sheath introducer, carries a slit elastic valve partition as part of the hemostasis valve. The inner housing has a bore and the end cap has an aperture that each communicate with an opposed surface of the valve partition. The diameter of the aperture and the bore are each of a distance that exceeds the outer diameter of preferably a french six catheter extending through the catheter of this invention, plus two times the thickness of the partition. When these conditions are satisfied, larger diameter inner catheters can be slidably inserted and removed through the catheter and valve of this invention with reduced frictional characteristics. Also, a compression ring is provided between the valve partition and the end cap which causes the valve partition to bow outwardly against the end cap and toward the aperture thereof. This, in turn improves the sealing characteristics. Also, an improved slit design for the partition is disclosed.

23 Claims, 1 Drawing Sheet

CATHETER HEMOSTASIS VALVE

BACKGROUND OF THE INVENTION

U.S. Pat. Nos. 4,798,594 and 4,895,565, among others such as Stevens U.S. Pat. Nos. 4,000,739 and 4,421,296, disclose catheter hemostasis valves which are mounted in a housing on the end of a catheter, typically a catheter sheath introducer. Such a catheter is used to facilitate the introduction of other catheters and guidewires into the vascular system of a patient, while minimizing injury to the patient at the access site. This is particularly used in situations where one or more catheters are inserted into and removed from the patient repeatedly, for example as in angioplasty. The presence of the catheter sheath introducer causes the trauma to the body to be limited to only one catheter entering at the body access site. All other catheters and guidewires pass through the catheter introducer, and thus are not traumatic to the body at the access site.

Catheter sheath introducers are known to carry a hemostasis valve which comprises a slit elastomeric partition or membrane carried in a housing. While the prior art shows many different designs of such membrane type hemostasis valves, there is still a desire for improvement in the performance of such valves with respect to their ability to seal against leakage of blood, as catheters and guidewires of varying diameters are passed through the valve. Also, it is important for the friction encountered as one advances a catheter or a guidewire through a catheter sheath introducer to be as low as possible. By this invention, improvements in both the sealing characteristics of the membrane valve of this invention and the frictional characteristics of the valve are achieved, to provide a partition valve for a catheter which exhibits improved characteristics over the prior art.

Furthermore, difficulties in resealing and friction are particularly encountered among the larger diameter catheters, for example catheters of a french six size and greater. By this invention a hemostasis valve is provided which is particularly capable of providing improvements in reducing friction and in the resealing of the valve, when used in conjunction with such larger diameter catheters.

DESCRIPTION OF THE INVENTION

In accordance with this invention, a catheter is provided which carries a hemostasis valve on one end thereof. The hemostasis valve comprises: an inner housing which is carried by the catheter end, an end cap or end wall carried by the inner housing, and a slit, elastic valve partition peripherally seated between the end cap or wall and the inner housing.

The inner housing has a bore, while the end cap or end wall has an aperture, each of which communicate with an opposed major surface of the valve partition. Preferably, the valve partition is made of an elastomer such as silicone rubber.

In one aspect of this invention, the catheter valve is intended to receive a catheter of six french or larger diameter. By this invention, the aperture of the cap has a diameter which is greater than the sum of the diameter of the six french (or larger) catheter, plus two times the thickness of the slit valve partition. Under these circumstances, as the catheter is withdrawn, the aperture of the cap is large enough to allow the elastic partition to rearrange itself about the slit to substantially its initial configuration. In prior art systems, withdrawal of a larger catheter can cause "bunching" of the partition valve, in which portions of the valve defined around the slit, especially when multiple radial slits are provided as is preferred, become distorted and fail to retract back to their original configuration. In this prior art circumstance, not only does the friction of the advancing or retracting catheter go up substantially, which is undesirable, but leakage may occur because of the distortions created in the elastomeric valve partition about the slit. However, significant improvements are provided when the cap aperture is larger than the above described limiting diameter, so that a hemostasis valve partition may accommodate catheters of six french, nine french, or greater with low friction and good sealing.

Additionally, it is preferred for the diameter of the bore of the inner housing adjacent to the valve, partition to exhibit the same diameter relationship as the aperture of the cap or end wall. Specifically, for a six french catheter the diameter of the bore adjacent the catheter is greater than the diameter of the six french catheter (0.078 inch) plus twice the thickness of the partition, which thickness is preferably about 0.04 to 0.08 inch. Thus for a six french catheter occupying the hemostasis valve of this invention, it is preferred for both the diameter of the bore adjacent the valve partition and the diameter of the cap aperture to be more than 0.178 inch, when the thickness of the partition is 0.05 inch.

For a nine french catheter occupying the valve,, the diameter of the partition and the bore adjacent the partition may be at least 0.22 inch to achieve the desired improvement.

Under these circumstances, significant improvements in frictional characteristics are achieved, as well as improved sealing characteristics of the catheter during and after receiving a catheter of six to nine french size or above.

In another aspect of this invention, the hemostasis valve may have a compression ring which is carried between the cap and the valve partition in a relation essentially surrounding and outside of the end cap aperture and housing bore, although it is understood that the respective components are in different planes. The compression ring is of a larger inner diameter than the aperture and the adjacent bore, and is of no more than equal diameter to the partition. The compression ring serves to press an annular, peripheral portion of the elastomeric partition against the housing. This causes a central portion of the valve partition to bow outwardly against the end cap, toward the aperture. The effect of this bowing is to reduce leakage from the valve by pushing together a portion of the slit on the inner side of the gasket. Thus, hemostasis is substantially improved by the addition of such a compression ring, particularly in the circumstance where the bore adjacent the partition is of less diameter than the inner diameter of the compression ring.

In another aspect of this invention, the slit of the elastic valve partition preferably comprises at least one generally helical first slit section extending from one side of the partition part way through the partition, and a second, spiral section of less diameter extending from the first slit section to the other side of the partition. The second, spiral slit section is connected to the first slit section by a connecting slit section which is substantially perpendicular to the catheter longitudinal axis. The second, spiral slit section preferably tapers to a minimum diameter at the other side of the partition. This minimum diameter is preferably on the order of the diameter of a guidewire.

One function of the second slit section, which preferably faces outwardly from the housing and end cap, is to receive and center a guidewire when it passes through the valve partition. As disclosed in Davila et al. patent Application No. 08/255,340 filed Jun. 7, 1994, a small aperture extending partway through a valve partition can accomplish this purpose. By this invention, that aperture, and the complexities involved in its manufacture, can be dispensed with by providing the disclosed pair of spiral and helical slit sections, which sections may be cut by a single tool of corresponding shape, so that guidewires may be easily centered while extending through the hemostasis valve even after the valve has been used to receive larger catheters. By this means, sealing is improved.

Preferably the first and second slit sections each comprise cross sections defining a plurality of radial, connected slit lines. Also, it is preferred for the first slit section to extend more than half way through the elastomeric valve partition, for example about two-thirds or three-quarters of the way. The second slit section may have a maximum diameter of about 0.2 inch, while the first, helical slit section has a minimum diameter of about 0.02 inch.

DESCRIPTION OF SPECIFIC EMBODIMENTS

Figure 1:
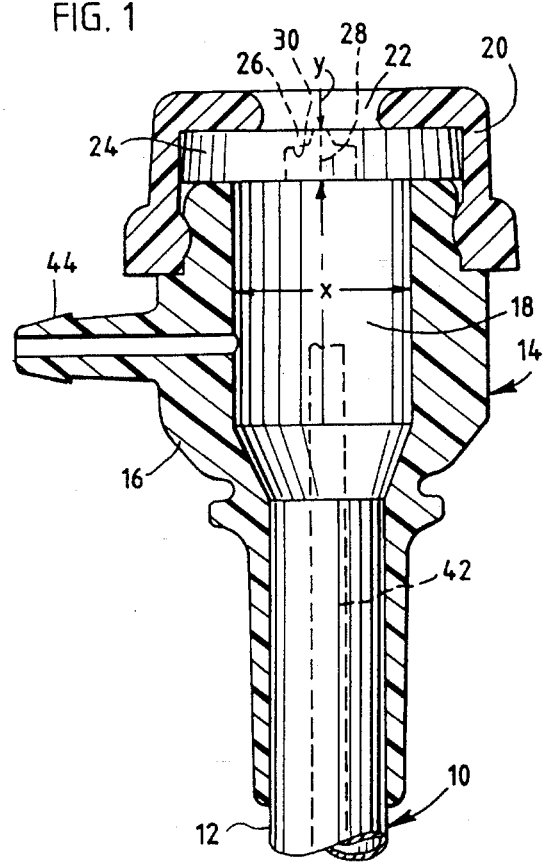
FIG. 1 is a fragmentary, longitudinal section view of a catheter introducer which carries the hemostasis valve of this invention.

Referring to the drawings, FIG. 1 shows a portion of a catheter sheath introducer which is of conventional construction except as otherwise indicated herein. Catheter introducer 10 comprises a tubular catheter 12 which carries a hub 14 on one end thereof. Hub 14, in turn, defines an inner housing 16 having a bore 18 that communicates with the bore of catheter body 12. Inner housing 16 is closed by an end cap 20, which is of a conventional design, being snap-fit and/or heat sealed into the disclosed position on inner body 16. End cap 20 defines a central aperture 22.

Catheter inner body 16 defines the typical side port 44 found in catheter introducers.

A slit elastomeric valve partition 24, typically a circular disk, is retained at its periphery with a pressure seal imposed between inner body 16 and end cap 20, as shown. Slit 26 of valve partition 24 may be of any known design, but preferably it comprises a plurality of radii 32 (FIG. 2) extending out from origin line 28 and extending through partition 24. Radii 32 are rotated in helical manner as they extend through the partition to form a generally helical first slit section 30 extending from the inner side of partition 24 for a distance of about two-thirds to three-quarters of the overall thickness of partition 24. Such thickness may be preferably about 0.05–0.07 inch. This helical structure is similar to that disclosed in Hillstead U.S. Pat. Nos. 4,798,594 and 4,895,565 except that they do not extend entirely through the elastomeric partition valve 24. Instead, a second, spiral section 40 of less diameter extends from the first slit section to the other, outer side 38 of partition 24. The second spiral slit section 40 is connected to the first slit section 30 by connecting slits 36 that are substantially perpendicular to the catheter longitudinal axis, so that the two slit sections are connected, although of significantly different diameters. Also, second, spiral slit section 40 tapers to a minimum diameter at the outer side 38 of partition 24.

Figure 2:
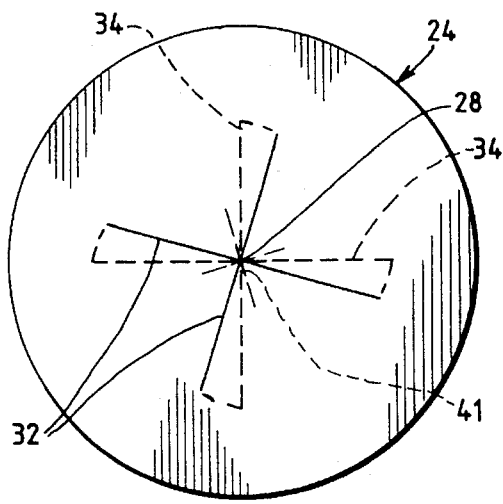
FIG. 2 is an enlarged plan view of the valve partition used in the valve of FIG. 1.

FIG. 2 shows partition 24 as seen from the underside of the partition as shown in FIG. 1 but excluding the other parts. In this particular embodiment, one would see a slit 32 of cross shape on the underside surface. However, as the slit cross 32 extends into the partition 24, the slit rotates in helical manner as stated above until the end of section 30 is reached, at which point the slit may be in the position shown in the dotted lines 34. At that point, each slit defines a radial slit line 36 (FIG. 3) which comprises the connecting slit portion which is substantially perpendicular to the catheter longitudinal axis as discussed above. Actually, radial slit lines 36 do not have to be specially made, but tend to be naturally formed by the shape of the slitting tool, which may be of a type similar to that disclosed in the above cited patents.

Figure 3:
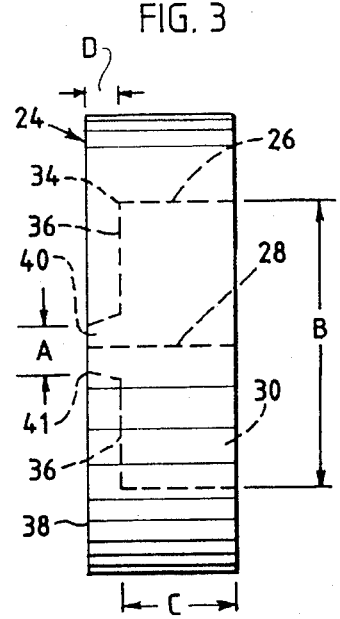
FIG. 3 is an elevational view of the valve partition used in FIG. 1.

Then, connected to slit lines 36 are a plurality of spiral slits which, in cross section form a cross-shaped slit line similar to lines 32, 34 except that they are of diminishing diameter as one approaches the outer surface 38 (FIG. 3) of valve partition 24, as shown in FIG. 3. This comprises the second spiral slit section 40 discussed above. As FIG. 2 shows, the twist continues, but in a spiral, not a helical manner in the second section so that the diameter of the radial slit line 41 at surface 38 is at its minimum.

As has been previously disclosed in the cited patent application, advantages can be achieved by the presence of a central, small diameter hole that extends partway through an elastomeric valve partition and engages a slit which extends the rest of the way through. Such a hole can be used to center a guidewire extending through the partition. Such centering of the guidewire facilitates the sealing against leakage around the guidewire after the partition has been stretched by previously receiving a larger catheter. By this invention, it has been found that a similar advantage is obtainable without the need for a hole by the user of the reduced-diameter, second slit section 40 as described herein.

Specifically, referring to FIG. 3, in a partition 24 having a thickness of about 0.05–0.07 inch, and a diameter of about 0.306–0.314 inch, dimension A may be about 0.035 inch or less; dimension B may be about 0.1–0.18 inch; dimension C may be about 0.02–0.04 inch (i.e., the depth of the first slit section); and dimension D (the depth of the second slit section) can be about 0.02–0.035 inch. Broadly, the thickness of such a gasket may typically range from 0.04–0.075 inch.

While the specific slit pattern shown comprises four radii in a cross pattern that extend first in a helical and then a spiral pattern, it is to be understood that other helical and spiral slit arrays may also be used. For example, from 3 to 6 slit radii may be used in the helical-spiral array as desired. Also reduced-diameter slit section 40 may be helical like the first section 30, not spiral.

Referring again to FIG. 1, both the enlarged bore portion 18 adjacent to valve partition 14 and aperture 22 of the end cap are larger than a certain minimum diameter, which is defined by the predetermined maximum dimension of a catheter 42 or other elongated member which is to penetrate catheter introducer 10 and valve partition 24. Specifically, catheter 42 may be at least of french six size, which corresponds to an outer diameter of 0.078 inch. If the valve of this invention is intended to receive such a french six catheter 42, or a larger catheter as the predetermined maximum catheter size, then the diameter X of the bore portion 18 adjacent partition 24 will by this invention exceed the outer diameter of catheter 42 by more than twice the thickness Y of partition 24. It should be noted that FIG. 1 is not to scale. The thickness Y of partition 24 is exaggerated for purposes of clarity.

The same relationship holds true relative to the preferred diameter of aperture 22, although the diameters of bore portion 18 and aperture 22 do not have to be identical. They are in accordance with this invention of a diameter in excess of the outer diameter of the largest expected catheter 42 to be received plus twice the thickness Y. When this condition is present, a significant reduction in the frictional forces is experienced when one attempts to insert a catheter 42 through the catheter introducer of this invention. While problems are not normally encountered with small catheters or a guidewire, this problem has been significant when catheters of french six size and above, are inserted into catheter 10 especially catheters of french seven size and above.

Thus, an improved catheter sheath introducer is provided by the above invention, in which large diameter catheters may be inserted through the catheter introducer 10, with significant improvements in the reduction of friction, along with high quality sealing. For example, when catheter 42 is of seven french size, aperture 22 may preferably have a diameter of 0.210–0.230 inch, while dimension X of bore portion 18 may be about 0.01–0.02 inch larger, for a valve partition having a thickness of about 0.04–0.07 inch.

Figure 4:
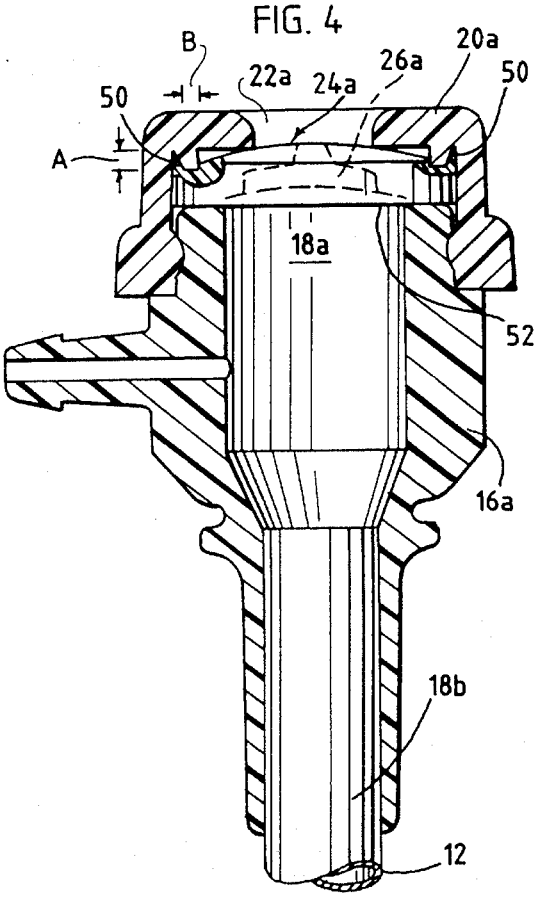
FIG. 4 is an enlarged fragmentary longitudinal sectional view of another embodiment of a catheter introducer and hemostasis valve of this invention.

Referring to FIG. 4, another embodiment of the catheter introducer of this invention is disclosed, being of similar construction to that of the previous embodiment except as otherwise disclosed herein.

Inner housing 16a is carried on an end of the catheter body 12a, and is closed off by an end cap 20a to peripherally retain a slit, elastomeric valve partition which may have a slit 26a of a design similar to that of the previous embodiment.

Further in accordance with this invention, a compression ring 50 is carried between end cap 20a and valve partition 24a, with the compression ring 50 surrounding the end cap aperture 22a and the portion 18a of the housing bore which is adjacent to partition 24a, in the sense that compression ring 50 is of larger inner diameter than aperture 24a and bore portion 18a. Also, compression ring 50 is of no more than equal diameter to the partition in the sense that is must engage the partition peripherally to press a peripheral portion of the partition to a greater degree than the rest of the end cap 20a presses the partition, such pressing being against the housing 16a. The effect of this, when the inner diameter of ring 50 is greater than the diameter of bore portion 18a, is to cause partition 24a to bow outwardly as shown in FIG. 4, and particularly to project outwardly to a degree into aperture 22a. This outward bowing is facilitated by the space provided underneath end cap 20a by the presence of ring 50.

The effect of such bowing enhances the sealing of the slit 26a, particularly in the portion adjacent the inner surface 52 of partition 24a. Thus, enhanced sealing is provided by the introducer catheter of FIG. 4.

Adjustment of the bowing of partition 24a can be made by variation of the dimensions of ring 50 and its respective diameter compared with the inner diameter of bore 18a. The bowing phenomenon is achieved primarily when the inner diameter of ring 50 is greater than the diameter of bore portion 18a.

Bore portion 18b may have a diameter less than bore portion 18a, being essentially the inner diameter of the catheter body 12.

The actual cross-sectional shape of segments of the ring 50 is not especially critical. However, it is preferred for the depth A (parallel to the catheter axis) of ring 50 to be about 0.015–0.03 inch. The radial width B of the segments of ring 50 (not the diameter) is similarly about 0.015 to 0.03 inch. The inner diameter of ring 50 is preferably about 0.21–0.27 inch, as compared to a preferred diameter of bore portion 18a being about 0.018–0.024 inch and less than the inner diameter of ring 50 as stated above. The preferred distance from the outer end of inner housing 16a to the inner surface of end cap 20a, where ring 50 engages the end cap, is preferably about 0.06–0.08 inch, and somewhat greater than the desired thickness of slit partition 24a, to make room for the bowing effect as illustrated in FIG. 4.

Thus a catheter is provided having a hemostasis valve on one end typically for use as a catheter introducer. Numerous improvements are exhibited by the catheter of this invention, particularly relating to the reduction of friction of larger diameter catheters inserted into the catheter introducer of this invention, while also improving the sealing.

The above has been offered for illustrative purposes only, and is not intended to limit the scope of the invention of this application, which is as defined in the claims below.

That which is claimed is:

1. A catheter which carries a hemostasis valve on one end, said hemostasis valve comprising: a housing which is carried by said catheter end, an end wall carried by said housing, and a slit elastic valve partition peripherally sealed between said housing and end wall, said housing having a bore and said end wall having an aperture that each communicate with an opposed, major surface of said valve partition, said catheter receiving an elongated member of predetermined maximum transverse dimension extending through said housing, end wall, and slit elastic valve partition, the diameter of said bore adjacent said valve partition being of a distance which is toward said aperture.

2. The catheter of claim 1 in which said predetermined maximum transverse dimension is at least the diameter of a french 9 catheter, said adjacent bore and aperture each having a diameter of at least 0.22 inch.

3. The catheter of claim 1 in which a compression ring is carried between said end wall and said valve partition in a relation essentially surrounding said end wall aperture and said housing bore, said compression ring being of larger inner diameter than said aperture and adjacent bore, and of no more than equal diameter to said partition, said compression ring pressing an annular, peripheral portion of said partition against said housing, causing a central portion of said valve partition to bow outwardly against said end wall toward said aperture.

4. The catheter of claim 1 in which the slit of said elastic valve partition comprises at least one generally helical first slit section extending from one side of said partition partway through said partition, and a second, spiral slit section of less diameter than the first slit section and extending from said first slit section to the other side of said partition, said second spiral slit section being connected to said first slit section by a connecting slit portion substantially perpendicular to the catheter longitudinal axis, said second slit section tapering to a minimum diameter at the other side of said partition.

5. The catheter of claim 4 in which said first and second slit sections each comprise cross sections defining a plurality of radial, connected slit lines.

6. The catheter of claim 5 in which said first slit section extends more than half way through said elastic valve partition.

7. The catheter of claim 5 in which said second slit section has a minimum diameter of no more than 0.035 inch.

8. The catheter of claim 5 in which said first slit section has a diameter of 0.1 to 0.18 inch.

9. The catheter of claim 1 in which the diameter of said aperture is also of a distance which is greater than the sum of said maximum transverse dimension of said elongated member plus twice the thickness of said valve partition.

10. A catheter which carries a hemostasis valve on one end, said hemostasis valve comprising: a housing which is carried by said catheter end, an end wall carried by said inner housing, and a slit, elastic valve partition peripherally sealed between said end wall and housing, said housing having a bore and said end wall having an aperture that each communicate with an opposed major surface of said valve partition, said aperture having a diameter of more than 0.178 inch and said valve partition being of greater diameter than said aperture, whereby a catheter of at least 6 french diameter can be withdrawn through said valve while avoiding increased friction through partition bunching.

11. The catheter of claim 10 in which said bore adjacent said valve partition has larger diameter than said aperture.

12. The catheter of claim 11 in which said elastic valve has a thickness of about 0.05 to 0.08 inch.

13. A catheter which carries a hemostasis valve on one end, said hemostasis valve comprising: a housing which is carried by said catheter end, an end wall carried by said housing, and a slit elastic valve partition peripherally sealed between said end wall and housing, said housing having a bore and said end wall having an aperture, said bore and aperture each communicating with an opposed major surface of said valve partition, a second catheter of at least six french diameter extending through said first named catheter and hemostasis valve, a portion of the bore of said inner housing which is adjacent said valve partition having a diameter which is larger than the outer diameter of said second catheter plus two times the thickness of said valve partition, said valve partition being of greater diameter than said aperture, whereby said second catheter can be further inserted or withdrawn with relatively reduced friction.

14. The catheter of claim 13 in which a compression ring is carried between said end wall and said valve partition in a relation essentially surrounding said end wall aperture and said housing bore, said compression ring being of larger inner diameter than said aperture and bore, and of no more than equal diameter to said partition, said compression ring serving to press an annular, peripheral portion of said partition against said housing, causing a central portion of said valve partition to bow outwardly against said end cap toward said aperture.

15. The catheter of claim 13 in which the slit of said elastic valve partition comprises at least one generally helical first slit section extending from one side of said partition partway through said partition, and a second, spiral slit section of less diameter extending from said first slit section to the other side of said partition, said second spiral slit section being connected to said first slit section by a connecting slit portion substantially perpendicular to the catheter longitudinal axis.

16. The catheter of claim 15 in which said second spiral slit section tapers to a minimum diameter at the other side of said partition.

17. The catheter of claim 15 in which said first and second slit sections each comprise cross sections defining a plurality of radial, connected slit lines and said first slit section extends more than half way through said elastic valve partition.

18. The catheter of claim 17 in which a compression ring is carried between said end wall cap and said valve partition in a relation essentially surrounding said end wall aperture and said housing bore, said compression ring being of larger inner diameter than said aperture and adjacent bore, and of no more than equal diameter to said partition, said compression ring serving to press an annular, peripheral portion of said partition against said housing, causing a central portion of said valve partition to bow outwardly against said end wall toward said aperture.

19. The catheter of claim 13 in which said aperture also has a diameter which is larger than the outer diameter of said second catheter plus two times the thickness of said valve partition.

20. A catheter which carries a hemostasis valve on one end, said hemostasis valve comprising: a housing which is carried by said catheter end and an end wall carried by the housing; a slit, elastic valve partition peripherally sealed within said housing, said housing having a bore and said end wall having an aperture that each communicate with an opposed major surface of the valve partition; a compression ring carried between the end wall and valve partition in a relation essentially surrounding the end wall aperture and said housing bore, said compression ring being of larger inner diameter than said aperture and housing bore and of no more than equal diameter to said partition, said compression ring serving to press an annular, peripheral portion of said partition against said housing, causing a central portion of said valve partition to bow outwardly against said end wall toward said aperture.

21. A catheter which carries a hemostasis valve on one end, said hemostasis valve comprising: a housing which is carried by said catheter end, and an end wall carried by said housing; a slit, elastic valve partition carried within said housing, said housing having a bore and said end wall having an aperture that each communicate with an opposed major surface of said valve partition, the slit of said elastic valve partition comprising at least one generally helical first slit section extending from one side of said partition partway through said partition, and a second, spiral slit section of less diameter than the first slit section extending from said first slit section to the other side of said partition, said second spiral slit section being connected to said first slit section by a connecting slit portion substantially perpendicular to the catheter longitudinal axis, said second slit section tapering to a minimum diameter at the other side of said partition.

22. The catheter of claim 21 in which said first and second slit section each comprise cross sections defining a plurality of radial, connected slit lines.

23. The catheter of claim 22 in which said first slit section extends more than half way through said elastic valve partition.

* * * * *

UNITED STATES PATENT AND TRADEMARK OFFICE
CERTIFICATE OF CORRECTION

PATENT NO. : 5,520,655
DATED : May 28, 1996
INVENTOR(S) : Luis A. Davila, Carlo R. De La Mata It is certified that error appears in the above-indentified patent and that said Letters Patent is hereby corrected as shown below:

Column 6, line 39, delete "toward said aperture." and substitute -- greater than the sum of said maximum transverse dimension plus twice the thickness of said valve partition. --

Signed and Sealed this

Twenty-third Day of September, 1997

Attest:

BRUCE LEHMAN

*Attesting Officer*     *Commissioner of Patents and Trademarks*